United States Patent
Snell

(10) Patent No.: US 6,263,245 B1
(45) Date of Patent: Jul. 17, 2001

(54) SYSTEM AND METHOD FOR PORTABLE IMPLANTABLE DEVICE INTEROGATION

(75) Inventor: Jeffery D. Snell, Oak Park, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/372,967

(22) Filed: Aug. 12, 1999

(51) Int. Cl.$^7$ ........................................... A61N 1/36
(52) U.S. Cl. ........................ 607/60; 607/32; 128/903
(58) Field of Search .............................. 607/27, 32, 60, 607/59; 128/903

(56) References Cited

U.S. PATENT DOCUMENTS

| | | | |
|---|---|---|---|
| 3,991,747 | 11/1976 | Stanly et al. | 128/2.06 R |
| 4,596,255 | 6/1986 | Snell et al. | 128/697 |
| 4,625,730 | 12/1986 | Fountain et al. | 128/419 D |
| 4,712,179 | 12/1987 | Heimer | 364/417 |
| 4,791,936 | 12/1988 | Snell et al. | 128/697 |
| 5,123,419 | 6/1992 | Platt et al. | 128/697 |
| 5,336,245 | 8/1994 | Adams et al. | 607/32 |
| 5,383,915 | * 1/1995 | Adams | 607/60 |
| 5,413,594 | 5/1995 | Williams | 607/32 |
| 5,522,396 | 6/1996 | Langer et al. | 128/696 |
| 5,626,630 | * 5/1997 | Markowitz et al. | 607/60 |
| 5,683,432 | 11/1997 | Goedeke et al. | 607/32 |
| 5,752,976 | 5/1998 | Duffin et al. | 607/32 |
| 5,759,199 | 6/1998 | Snell et al. | 607/60 |
| 5,899,931 | * 5/1999 | Deschamp et al. | 607/60 |
| 6,141,588 | * 10/2000 | Cox et al. | 607/9 |

* cited by examiner

Primary Examiner—Carl Layno

(57) ABSTRACT

A system and method for obtaining data from an implantable medical device and delivering the data to a data processing device is disclosed. A portable interrogation device conducts a wireless interrogation of an implantable medical device implanted in a patient, and stores the data received from the implantable device in a memory of the portable interrogation device. At a later time, the portable interrogation device is directly interfaced with a data processing device using a high-speed connection, which provides the data processing device with high speed access to the interrogated data that is stored in the portable interrogation device's memory.

44 Claims, 5 Drawing Sheets

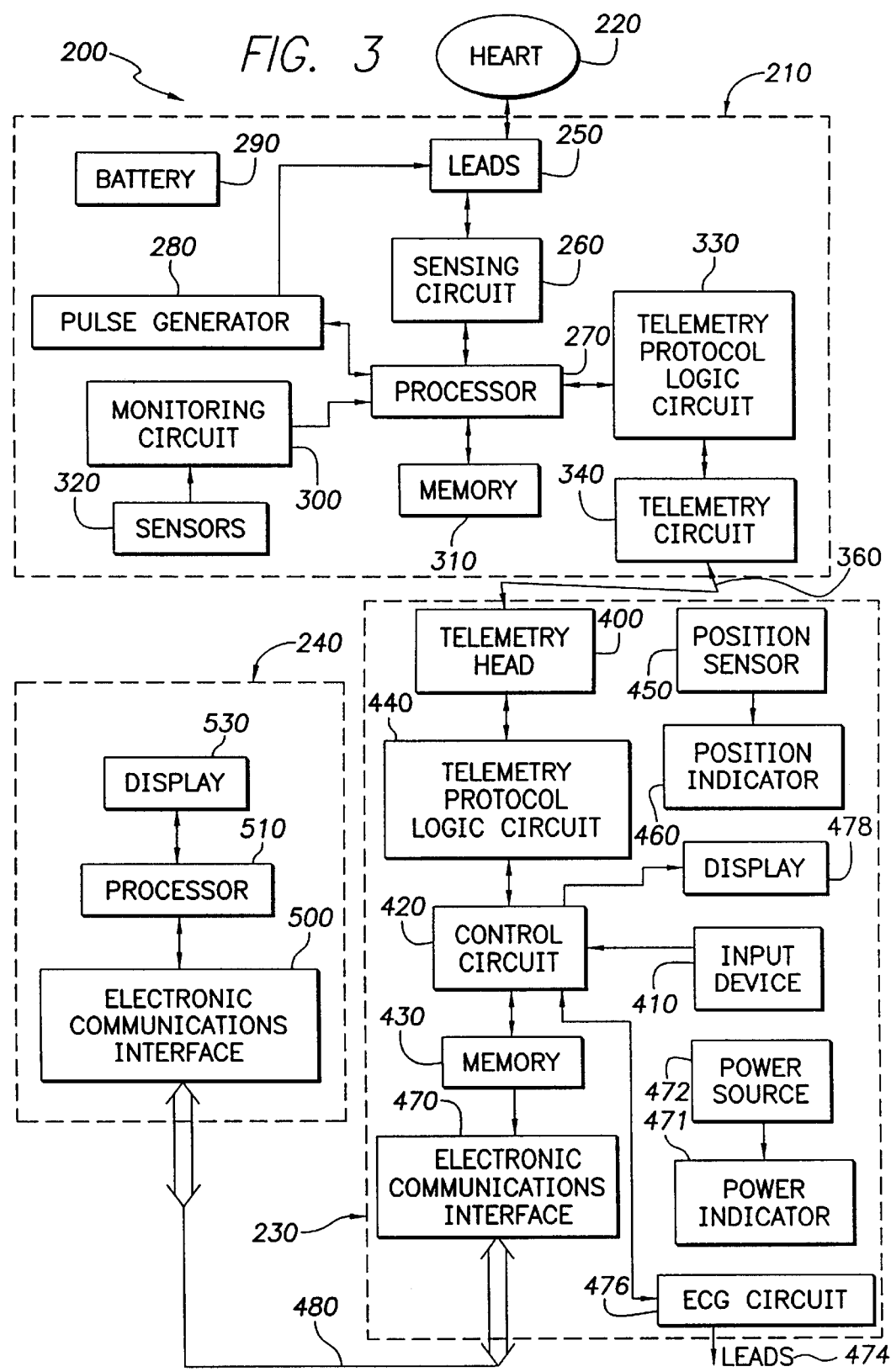

SYSTEM AND METHOD FOR PORTABLE IMPLANTABLE DEVICE INTEROGATION

FIELD OF THE INVENTION

The present invention relates to a system and method for obtaining medical data from an implantable medical device and delivering the data to a data processing device.

BACKGROUND OF THE INVENTION

Implantable medical devices are implanted in a patient's body to diagnose and treat a wide variety of medical conditions. One type of implantable medical devices is implantable cardiac stimulating devices, which detect and treat cardiac arrhythmias by applying electrical stimulation to the heart.

There are several types of implantable cardiac stimulating devices, each designed to treat a specific type of arrhythmia. One such device is a cardiac "pacemaker," which is used to treat an abnormally slow heart rate, a condition known as bradycardia. A cardiac pacemaker administers electrical "pacing pulses" to the heart in order to regulate the beating of the heart so that it will properly perform the physiological function of the heart.

While early models of pacemakers delivered pacing pulses at a consistent, predetermined rate, some types of modern pacemakers pace at a controlled variable or intermittent rate depending on the needs of the patient. For example, "demand pacemakers" can sense the patient's intrinsic heart rate and will deliver pacing pulses only when the intrinsic heart rate falls below a predetermined threshold rate. This threshold rate typically is a programmable parameter that is set by a physician in accordance with the physiological requirements of the patient, often determined by testing and monitoring of the patient at the physician's office.

Another type of pacemaker, the "rate-responsive" pacemaker, has the capability of varying the rate of pacing pulses, and therefore varying the patient's heart rate, by sensing physiological characteristics of the patient in order to determine the appropriate heart rate at any point in time. For example, when the patient performs activities demanding physical exertion, motion sensors, such as, for example, accelerometers associated with the pacemaker, sense increased motion and cause the gradual increase of the rate of delivery of pacing pulses accordingly, in order to increase heart rate. Other parameters that may be sensed by the pacemaker include body temperature, body impedance, and sound. By allowing the heart rate to depend on physiological variables such as level of physical activity, rate-responsive pacemakers permit bradycardia patients to engage in physical activities that their illness would normally preclude.

Other types of implantable cardiac stimulating devices are used to detect and treat arrhythmias known as "tachycardia" and "fibrillation." Some of these devices can also treat bradycardia. In contrast to the abnormally slow heart rate symptomatic of bradycardia, tachycardia is a condition in which the patient's heart beats at a faster than normal rate. Tachycardia prevents the chambers of the heart from filling sufficiently with blood between beats, thereby adversely effecting the heart's performance. Devices called "cardioverters" are used to treat tachycardia by employing pacing pulses in special sequences known to be effective in treating tachycardia. Fibrillation is a severe and rapid beating of the heart, rendering it essentially ineffective as a pump, and is considered the most severe form of cardiac arrhythmia. Implantable devices used to treat fibrillation are known as "defibrillators," and deliver high-energy shocks to the heart.

Devices called "implantable cardioverter-defibrillators," or "ICDs," treat both tachycardia and fibrillation. ICDs employ a variety of electrical means to alter the pacing of the heart based on the severity of the detected arrhythmia. A commonly used approach is "tiered therapy," whereby the aggressiveness of the electrical stimulation is increased as the severity of an arrhythmia episode increases and as less aggressive therapies fail.

Implantable cardiac stimulating devices acquire and store various types of data in order to administer therapy properly to the patient. For example, sensory data relating to physiological conditions is collected. Sensory data can include information pertaining to the patient's activity level or cardiopulmonary needs, to the mechanical activity of the patient's heart such as cardiac wall motion data, or to an intracardiac electrogram (IEGM) sensed through leads to the patient's heart. For example, in a "dual-chamber" device, leads are connected to the atrium for sensing P waves and to the ventricle for sensing R waves, and one or both of these waves may be recorded by the implantable device. A related type of data represents the occurrence of cardiac events and the response of the device thereto ("marker" data). Yet another type of data indicates the status of operational parameters of the implantable device, including battery voltage, battery impedance, and lead integrity data.

Performance of the implantable device is controlled by programmable parameters stored in the device. The programming and analysis of an implantable cardiac stimulating device is typically an ongoing process involving periodic supervision by a physician, in which the physician obtains the sensory, marker, and/or operational data and, based on an analysis of this data, evaluates the performance of the implantable device. Based on the performance of the device and the patient's medical condition as indicated by the data, the physician may reprogram parameters stored in the implantable device, thereby optimizing performance of the device.

A data processing device such as a "programmer/analyzer" is used by the physician for analyzing the data obtained from the implantable medical device, and/or for computing appropriate values for programmable parameters for the device. In prior art systems, the programmer/analyzer typically communicates with the implantable device using wireless telemetry. Wireless telemetry allows noninvasive communication of stored data from the implanted device to the programmer/analyzer subsequent to implantation of the device, such as during patient follow-up visits. The programmer/analyzer conducts an "interrogation" of the implantable device by causing a message to be sent to the implantable device using wireless telemetry, directing the implantable device to transmit data back to the programmer/analyzer or to collect data, or both. Typically, a telemetry head included on a "telemetry wand" is used for the interrogation. The telemetry wand is held close to the patient's chest during interrogation and is wired to the programmer/analyzer.

The implantable device responds to the interrogation by assembling the requested data, formatting it for telemetric transmission, and transmitting it back to the programmer/analyzer using wireless telemetry. The programmer/analyzer receives the data and uses it to analyze the performance of the device and, if necessary, compute appropriate adjustments to the device's programmable parameters. The programmer/analyzer can then re-program the implantable device by transmitting a message adjusting its programmable parameter(s). Thus, by analyzing data obtained by interrogation of the implantable device, the physician can noninvasively monitor and optimize the performance of the device on a regular basis.

SUMMARY OF THE INVENTION

The present invention is directed to a portable interrogation device for obtaining medical data derived from or stored by an implantable medical device implanted in a patient and delivering the data to a data processing device such as a programmer/analyzer. The invention has application for interrogation and programming of implantable cardiac devices, but is not so limited. The device makes use of a control circuit for controlling transmission of interrogation signals to an implantable device using telemetry, a transmitter for sending the signals, a receiver for receiving data transmitted by the implantable device in response to the interrogation signals, a memory for storing the data received, and an electronic communications interface for high-speed delivery of the data to the data processing device.

There are several problems or limitations in the known systems for interrogation of an implantable medical device. For example, while the use of telemetry to transmit data from the implantable device to the programmer/analyzer may be noninvasive, it is relatively slow. Valuable time of both the patient and physician is wasted by requiring the patient to come to the clinic, wait for the physician to become available, go to the examining room where there is a programmer/analyzer connected to a telemetry wand, and remain there while the physician conducts the interrogation. Likewise, the physician is inconvenienced by the slow process of acquiring the data telemetrically from the implantable device, a process which may take anywhere from three to five minutes, and having to be present for at least part of the interrogation.

A more efficient system of interrogation could allow the patient to conduct the interrogation on his own time, at his own convenience, and allow for the storage of the data and subsequent high-speed access to the data by the physician using a programmer/analyzer at the physician's convenience, during the patient's visit or otherwise. Another limitation to known systems for interrogation is that the programmer/analyzer must be present during the interrogation, in order to direct the interrogation and receive the data. This presents limitations as to where, when, and sometimes even how the interrogation may occur.

Thus, a system of interrogating an implantable device to obtain the data collected by the device and to store the data for later, high-speed access by a programmer/analyzer, is desirable. Such a system could avoid the need for the physician to be present during an interrogation, as well as the need for a complete implantable device programmer/analyzer to be in the room during interrogation, and allow the physician to access the stored data quickly, using a programmer/analyzer at his own convenience.

In a first embodiment, the present invention provides a system for the communication of medical data comprising an implantable medical device that transmits medical data by wireless communication at a first data transmission speed; a portable interrogation device that receives the medical data transmitted by the implantable medical device, the portable interrogation device transferring at least a portion of the stored medical data at a second data transmission speed higher than the first data transmission speed via an electronic communication interface; and a data processing device, coupled to the electronic communication interface, that receives the stored medical data transmitted by the portable interrogation device at the second data transmission speed and processes the received medical data for analysis by a physician.

In a second embodiment, the present invention provides a portable medical data communications device comprising a control circuit that controls wireless transmission of interrogation instructions to an implantable medical device implanted in a patient; a transmitter that transmits the interrogation instructions to the implantable medical device upon direction of the control circuit; a receiver that receives data transmitted by the implantable medical device in response to the interrogation instructions, the data being transmitted by wireless communication at a first data transmission speed; a memory that stores the data received from the implantable medical device; and an electronic communications interface that delivers at least a portion of the stored data to a data processing device, the delivery of the stored data occurring at a second data transmission speed higher than the first data transmission speed.

In a third embodiment, the present invention provides a method of communicating medical data comprising transmitting interrogation instructions from a portable medical data communications device to an implantable medical device implanted in a patient using wireless communication; based on the interrogation instructions, receiving medical data from the implantable medical device at the portable medical data communications device at a first data transmission speed using wireless communication; storing the medical data in a memory at the portable medical data communications device; and, based on a request to access the stored medical data by a data processing device operatively coupled to the portable medical data communications device by an electronic communications interface, delivering at least a portion of the stored medical data to the data processing device at a second data transmission speed higher than the first data transmission speed.

In a fourth embodiment, the present invention provides a portable medical data communications device comprising a processor that controls transmission of instructions to an implantable medical device implanted in a patient; a transmitter that transmits by wireless telemetry the instructions to the implantable medical device upon direction of the processor; a receiver that receives by wireless telemetry data transmitted by the implantable medical device in response to the instructions, the data being transmitted at a first data transmission speed; a memory that stores the data received from the implantable medical device; and an electronic communications interface that operatively couples the memory to a communication path associated with a data processing device, the communication path being used for delivering at least a portion of the stored data from the memory to the data processing device at a second data transmission speed higher than the first data transmission speed.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 3 is a functional block diagram of a portable implantable device interrogation system;

Like reference numbers and designations in the various drawings indicate like elements.

DETAILED DESCRIPTION OF THE INVENTION

Figure 1:
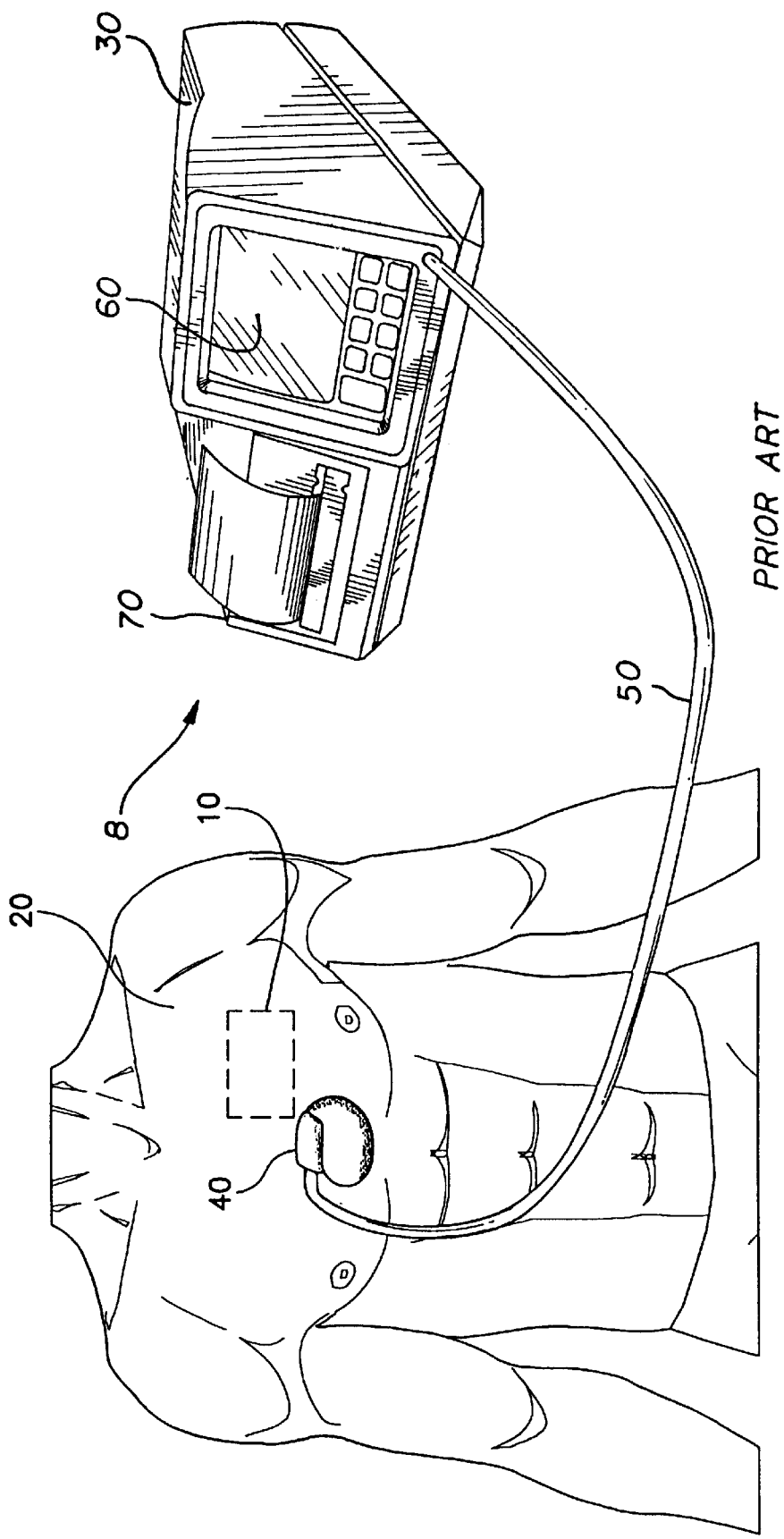
FIG. 1 is a diagram of a conventional programming and monitoring system for use with a medical device implanted in a patient.

FIG. 1 is a diagram of a conventional programming and monitoring system 8 for use with a medical device 10 implanted in a patient 20. The programming and monitoring system 8 includes a conventional programmer/analyzer 30 and a telemetry head 40 connected to the programmer/analyzer 30 by a communications cable 50.

In typical operation, telemetry head 40 is placed in close proximity to the medical device 10 in order to interrogate and/or program the medical device 10 by telemetric communication of data. The programmer/analyzer 30 directs the interrogation or the programming by transmitting data to and/or receiving data from the medical device 10 through telemetry head 40 by way of communications cable 50. The medical device 10 is programmed by sending instructions to the device which adjust the device's programmable parameters. Programmer/analyzer 30 can be used to program a variety of parameters of the medical device 10, including threshold rate, pacing pulse amplitude, and pacing pulse width in the case of a cardiac stimulating device. The programmer/analyzer 30 conducts an interrogation by sending the medical device 10 instructions to transmit certain data collected by the medical device.

Data interrogated can include: sensory data relating to physiological conditions such as the mechanical activity of the patient's heart (such as cardiac wall motion data), or electrical activity such as the patient's intracardiac electrogram (IEGM) sensed through leads to the patient's heart; the occurrence of cardiac events and the response of the device thereto ("marker" data); and operational parameters of the implantable device, including battery voltage, battery impedance, and lead integrity data. Additional types of data also can be interrogated. The programmer/analyzer 30 processes the data interrogated, and displays the data on monitor 60 or prints out hard copies on printer 70.

Interrogation using a system 8 as shown in FIG. 1 has several limitations. A first limitation is that communications cable 50 restricts the movement of the patient 20 during interrogation, which not only requires the patient to be in the same room as the programmer/analyzer 30 during interrogation and programming, but also limits the level of physical activity of the patient during interrogation and programming. Typically, the physician will desire to program the medical device 10 during a patient visit and then immediately test and observe the performance of the medical device 10 in response to the programming, in order to determine if further adjustments are needed. Thus, it is helpful and sometimes necessary for the patient 20 to perform strenuous physical activities while the medical device 10 is being monitored using the programming and monitoring system of FIG. 1. Communications cable 50 can restrict the types of activities the patient can perform.

A second limitation of the programming and monitoring system of FIG. 1 is that the process of delivering the data from the medical device 10 to the programmer/analyzer 30 requires several minutes, mainly due to the time required for the telemetric transmission of data between telemetry head 40 and medical device 10. The physician typically must supervise this process.

A third limitation of the programming and monitoring system of FIG. 1 is that the medical device 10 can be interrogated only upon the patient's visit to the physician. Since the medical device 10 has a small memory relative to programmer/analyzer 30, the amount of data that can be recorded before an interrogation acquires the data is limited, thus requiring frequent visits if the physician desires to collect and analyze a large amount of data. Thus, there is a need for a portable interrogation device which allows the patient to move freely during interrogation and programming, which delivers data at high speed to a programmer/analyzer, and which allows a patient to conduct an interrogation at his own convenience or choosing.

Figure 2:
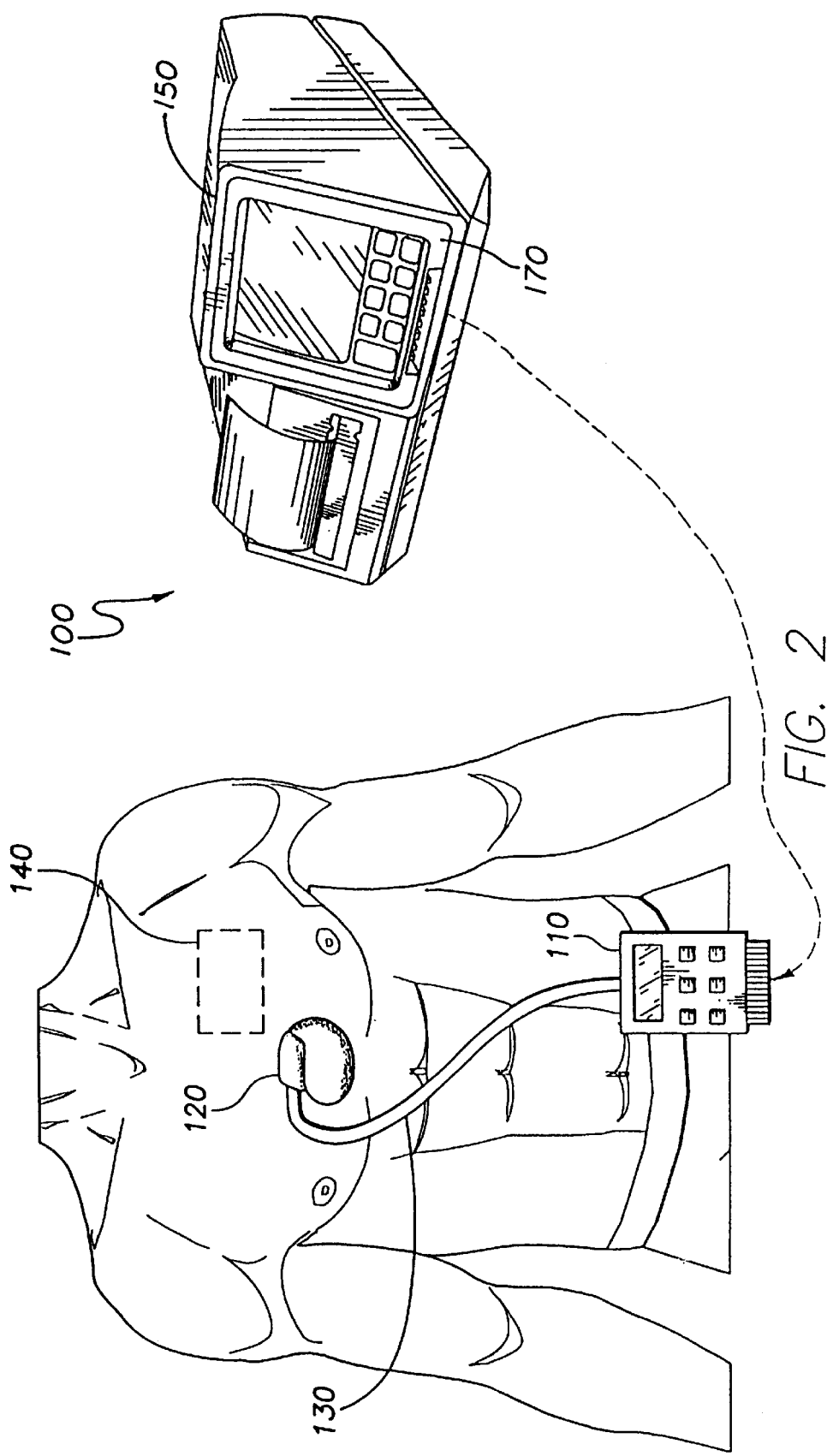
FIG. 2 is a diagram of an exemplary portable implantable device interrogation system of the present invention.

FIG. 2 is a diagram of an exemplary portable implantable device interrogation system 100 of the present invention. Portable implantable device interrogation system 100 includes portable interrogation device 110, medical device 140, and programmer/analyzer 150.

Portable implantable device interrogation system 100 transmits data to and receives data from medical device 140 through telemetry head 120, which is connected to portable interrogation device 110 by communications wire 130. Alternatively, telemetry head 120 may be incorporated in portable interrogation device 110. Typically, RF transmissions using a telemetry protocol are utilized to communicate data between medical device 140 and portable interrogation device 110. The data transmitted to the medical device 140 can include interrogation instructions or programming instructions, and in response the medical device can transmit any of the data or parameters discussed above such as, for example, stored sensory data.

Portable interrogation device 110 communicates with programmer/analyzer 150 through interface 160, by which the portable interrogation device 110 may be directly connected to programmer/analyzer interface 170. Thus, data obtained by portable interrogation device 110 from medical device 140 may be stored in portable interrogation device 110 during interrogation, and then at a later time portable interrogation device 110 may be connected to programmer/analyzer 150 to enable high speed access to the data by programmer/analyzer 150. In one embodiment, the portable implantable device interrogation system 100 includes a portable interrogation device 110 having a memory for storing data, and connecting the portable interrogation device 110 to the programmer/analyzer through interfaces 160 and 170 couples the memory to a processor in programmer/analyzer 150 via a wired communication interface. Thus, a processor of programmer/analyzer 150 can access the data obtained from medical device 140 at high speeds associated with the access of data in an integrated computer system via a wired communication interface, rather than the relatively slow speed of telemetric communication. Using a wired communication interface conforming to the RS-232 standard, data can be accessed at speeds on the order of 115,000 bits per second, using the Universal Serial Bus standard over 1 million bits per second, or using the Firewire standard around 8 million bits per second. In contrast, traditional telemetric communication associated with an interrogation occurs at speeds on the order of 8000 bits per second of "raw" data.

FIG. 3 is a functional block diagram of a portable implantable device interrogation system 200 of the present invention. Portable implantable device interrogation system 200 includes medical device 210 for applying, for example, electrical stimulation to a patient's heart 220 to treat arrhythmia; portable interrogation device 230 for interrogating and/or programming the medical device 210 and storing the data for later delivery; and data processing device 240 for receiving the stored data from portable interrogation device 230, processing the data, and displaying the data for analysis by a physician.

Medical device 210 is implanted in a patient and applies electrical stimulation to the patient's heart 220 through leads 250 in contact with the myocardium. Leads 250 also can be used to sense cardiac electrical activity and obtain IEGM data. Leads 250 send analog electrical signals representing this cardiac activity to sensing circuit 260 that amplifies and digitizes the received signals for use by a processor 270.

Processor 270 performs the functions required to analyze the electrical signals representing cardiac activity, detect the occurrence of an arrhythmia, classify the type of arrhythmia, and initiate the appropriate therapy. When processor 270 detects an arrhythmia (for example, using information obtained from monitoring circuit 300), processor 270 directs the pulse generator circuit 280 to generate a charge of particular energy sufficient to administer the therapy required. A battery 290 supplies power for charging the pulse generating circuit as well as for delivering power to the entire medical device 210. When the pulse generator circuit 280 has generated a sufficient charge, processor 270 directs the pulse generator 280 to deliver the charge to the heart 220 through the leads 250. This process is then repeated as necessary in accordance with the different types of arrhythmias and their treatments, discussed herein.

A monitoring circuit 300 monitors the operation of the medical device 210 and collects data pertaining to the operational parameters of the medical device 210 (such as battery voltage, current, and lead system impedance), sensory data relating to physiological conditions such as the mechanical activity of the patient's heart (such as cardiac wall motion data) or electrical activity (such as the patient's IEGM), and the occurrence of cardiac events and the response of the device thereto (marker data). Sensory data is collected by sensors 320 such as accelerometers, piezoelectric sensors, and/or body impedance sensors. The data collected by monitoring circuit 300 can be stored in a memory 310, for example at the direction of processor 270.

The medical device 210 includes a telemetry protocol logic circuit 330 that communicates with the processor 270. Telemetry protocol logic circuit 330 receives data from the processor 270 in response to, for example, interrogation instructions delivered to the medical device 210. The data could be stored data retrieved from memory 310 or data obtained contemporaneously through leads 250 or sensors 320. The telemetry protocol logic circuit 330 formats the data it receives into a first data format for telemetric transmission by converting the data into a serial bit stream, and then sends the bit stream to a telemetry circuit 340, which includes a transmitter and an antenna for wireless transmission of signals.

The telemetry circuit 340 uses the serial bit stream to modulate a signal in a conventional manner and transmits the modulated signal at a first data transmission speed via a first communication path 360. The modulated signal is received by an external telemetry head 400 associated with the portable interrogation device 230.

Telemetry circuit 340 also includes a receiver for receiving telemetry signals transmitted by external telemetry head 400. The telemetry signals received are delivered to telemetry protocol logic circuit 330, and converted for interpretation and use by processor 270 and/or monitoring circuit 300. Typically, an exchange of interrogation signals and interrogated data, which occur at the first transmission speed, takes up to five minutes.

Interrogation of the medical device 210 is performed by portable interrogation device 230. Interrogation can be initiated manually or automatically. A patient can initiate the interrogation by entering an input at input device 410 associated with portable interrogation device 230. Input device 410 can be a keyboard, keypad, button, switch, pointing device, voice recognition interface, or any other structure allowing the user to enter an input. Alternatively, the interrogation can be initiated when the portable interrogation device 230 detects an implantable device 210 by, for example, using position sensor 450 to sense electromagnetic induction of the implantable device. Portable interrogation device 230 can be pre-programmed to always transmit certain interrogation instructions in response to a simple input (such as the pressing of a button) in order to enable a patient to easily initiate an interrogation, for example before a visit to his physician's office or at the direction of his physician or immediately following an arrhythmia. Alternatively, the input device 410 for portable interrogation device 230 may be a variable input allowing the patient to indicate particular interrogation parameters. In response to an input, control circuit 420 initiates an interrogation. Control circuit 420 may be a microprocessor that follows interrogation instructions programmed in software stored in memory 430. Memory 430 can include RAM, ROM, or other memory types to store software instructions for operation of portable interrogation device 230 as well as rewritable memory for storage of data obtained from medical device 210. Control circuit 420 processes interrogation instructions and delivers the instructions to telemetry protocol logic circuit 440, which formats the instructions for telemetric transmission in a manner described above. The telemetry protocol logic circuit 440 relays the formatted instructions to telemetry head 400, which is placed on or near the patients body, near the medical device 210. Telemetry head 400 may be external to the portable interrogation device 230 and connected to portable interrogation device 230 by means of an external wire, for example, or may be incorporated in portable interrogation device 230. Telemetry head 400 includes a transmitter and antenna for wireless transmission of signals formatted by telemetry protocol logic circuit 330, and a receiver for receiving telemetry signals from telemetry circuit 340.

Telemetry head 400 transmits the formatted interrogation instructions to telemetry circuit 340 of medical device 210. Medical device 210 responds to the interrogation as described above by telemetrically transmitting the requested data back to portable interrogation device 230. The telemetry circuit 440 demodulates the telemetry signal received by telemetry head 400, extracts the serial bit stream, and formats the data in a second data format in a manner suitable for storage in memory 430 and subsequent access by data processing device 240. The control circuit then directs the data to be delivered to memory 430 for storage. The data is accessed later by data processing device 240 at a second data transmission speed through electronic communications interface 470. The second data transmission speed is greater than the first data transmission speed. For example, with an RS-232 interface, the second transmission speed may be at least ten times greater than the first transmission speed; with a USB interface, the second transmission speed may be at least 100 times greater than the first transmission speed; and with a Firewire interface, the transmission speed can be at least one thousand times greater than the first transmission speed. Electronic communications interface 470 may be implemented, for example, by an RS-232 serial interface or any other interface allowing portable interrogation device 230 to be connected to data processing device 240, e.g., via communication path 480 Alternatively, electronic communications interface 470 could be a medium for carrying a high-speed wireless transmission, allowing the portable interrogation device 230 to deliver the stored data to the data processing device 240 by wireless communication. Since portable interrogation device 230 is external to the patient, size is not as critical a concern as for the medical device 210, and thus memory 430 can be significantly larger (in terms of storage size and corresponding physical size) than memory 310 of medical device 210. Memory 430 can be realized in a variety of ways, such as RAM incorporated in the portable interrogation device 230, a PCMCIA memory card including an electronic communications interface, or removable media such as high-density diskettes. PCMCIA memory cards, removable media and the like are considered to be alternative implementations of the communication path 480 in that they can be alternatively be used to enable the high speed delivery of data from the portable interrogation device 230 to the data processing device 240.

Data processing device 240 is used by a physician for analyzing data obtained from medical device 210 and/or programming medical device 210. Typically, data processing device 240 is a programmer/analyzer. Data processing device 240 may or may not include its own telemetry circuit (not shown) for communicating directly with medical device 210. Data processing device 240 includes a processor 510 for processing data from medical device 210 and computing programmable parameters for medical device 210. Data processing device 240 can receive or access data at high speed through electronic communications interface 500, which can be connected to electronic communications interface 470 of the portable interrogation device 230, allowing the processor 510 to access the data stored in memory 430 of portable interrogation device 230. Preferably, electronic communications interfaces 470 and 500 are each associated with mechanical components such as pin connectors, spring connectors, or other components allowing portable interrogation device 230 to be interfaced with data processing device 240. Alternatively, if a PCMCIA memory or diskette is used as memory 430, electronic communications interface 500 is interfaced with the PCMCIA memory or diskette by removal of the PCMCIA memory card or diskette from portable interrogation device 230 and plugging the PCMCIA memory card or diskette into a slot or drive on data processing device 240 associated with the electronic communications interface 500.

When processor 510 requests some or all of the data from memory 430, the data is delivered to processor 510 over the high-speed communication path 480 at a second data transmission speed. Thus, a physician can instruct his patient to perform an interrogation using portable interrogation device 230 before the patient visits the physician, and upon arrival of the patient, the physician can almost immediately access the interrogated data by connecting the portable interrogation device to data processing device 240 through electronic communications interfaces 470 and 500. Alternate structures other than communication path 480 can be used to transfer the data from memory 430 to processor 510 at high speed. Display 530, including a display logic circuit, can be included in data processing device 240 for displaying the data for a physician, allowing the physician to analyze the performance of the medical device 210 and re-program its parameters accordingly.

In one implementation, portable implantable device interrogation system 200 can be used to program medical device 210. While portable interrogation device 230 and data processing device 240 are interfaced, a physician operating data processing device 240 can instruct processor 510 to deliver programming instructions to control circuit 420 of portable interrogation device 230. Control circuit 420 relays the programming instructions to telemetry protocol logic circuit 440, which formats the instructions for telemetric transmission. The telemetry head 400 is placed on the patient near the medical device 210. It may be necessary or desirable to remove portable interrogation device 230 from the data processing device 240. The input device 410 on the portable interrogation device 230 is activated, and the programming instructions are telemetrically transmitted from telemetry head 400 of the portable interrogation device 230 to telemetry circuit 340 of the medical device 210. The telemetry protocol logic circuit 330 of medical device 210 formats the programming instructions for use by the processor 270, and the processor 270 adjusts the programmable parameters of the medical device 210 accordingly.

Portable interrogation device 230 can include a position sensing circuit 450 that detects when the telemetry head 400 is sufficiently near the medical device 210 for an interrogation (by, for example, measuring the electromagnetic inductance of the medical device). Position sensing circuit 450 is coupled to a position indicator 460 that indicates to the patient initiating the interrogation whether the telemetry head 400 is in position for the interrogation to occur, and indicates during the interrogation if the telemetry head 400 has fallen out of position. Position indicator 460 can be, for example, an LED set, an LCD display, or an audio speaker. Portable interrogation device 230 also can include attaching or securing means such as straps, belts, clips, or adhesives to secure portable interrogation device 230 to the patient, and/or to secure telemetry head 400 near medical device 210. Portable interrogation device 230 is powered by a power source 472 such as a battery or other power source which may or may not be rechargeable. A power indicator 471 can accompany the power source 472 in order to indicate to a patient if the power source is depleted.

In addition to data obtained from medical device 210, portable interrogation device 230 can obtain ECG data from the patient. Portable interrogation device 230 can include leads 474 that are connected to the patients skin, and an ECG circuit 476, collectively used to obtain the patient's ECG. Portable interrogation device 230 can also include ECG display 478 to display the resulting ECG. Furthermore, control circuit 420 of portable interrogation device 230 can include a synchronization circuit for synchronizing cardiac data obtained from the patient and the implantable device 210, such as marker data, electrogram data, and ECG data. Examples of such synchronization circuits are described in U.S. Pat. No. 4,791,936 entitled "Apparatus for Interpreting and Displaying Cardiac Events of a Heart Connected to a Cardiac Pacing Means," incorporated herein by reference; and U.S. Pat. No. 4,596,255 entitled "Apparatus for Interpreting and Displaying Cardiac Events of a Heart Connected to a Cardiac Pacing Means," also incorporated herein by reference.

Figure 4A:
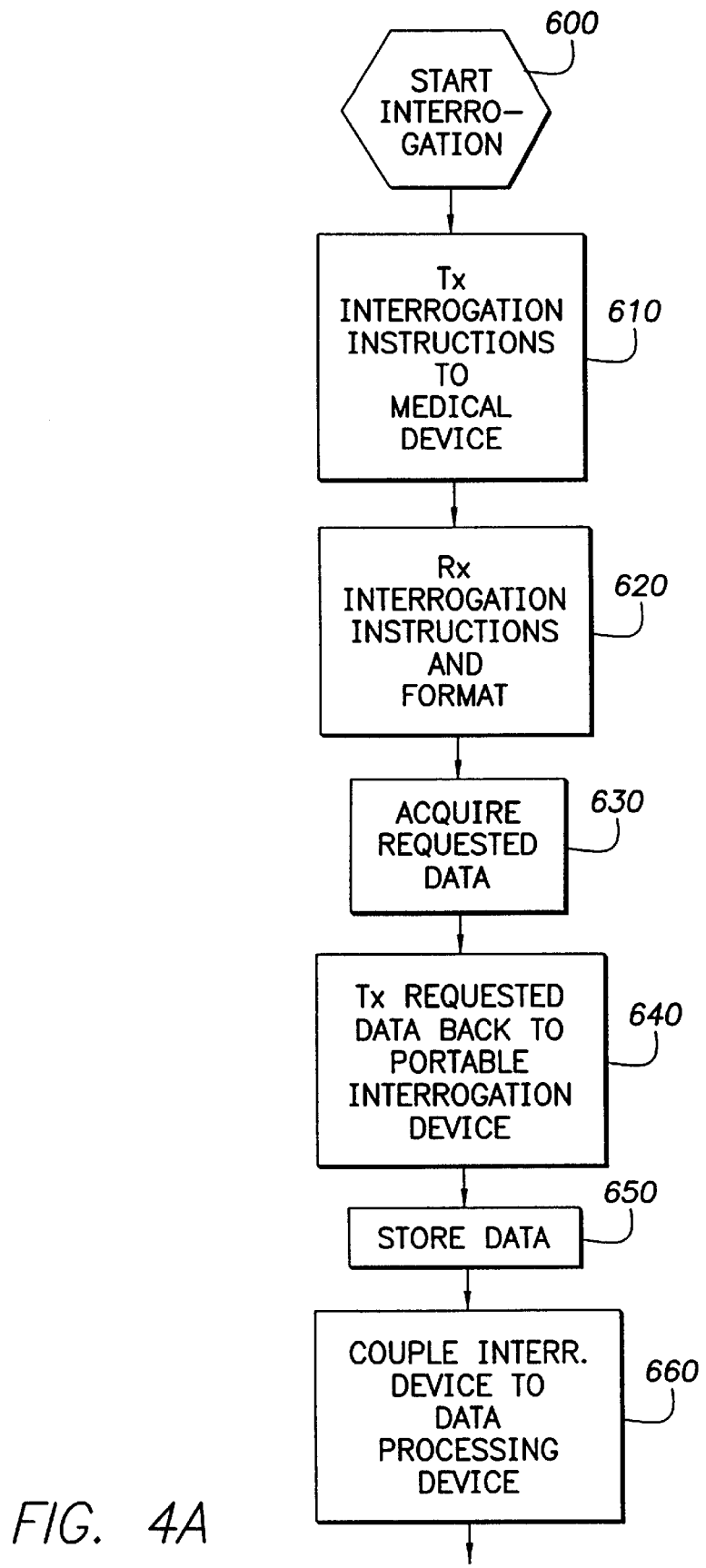
FIG. 4A is a flow diagram illustrating the operation of a portable implantable device interrogation system.
Figure 4B:
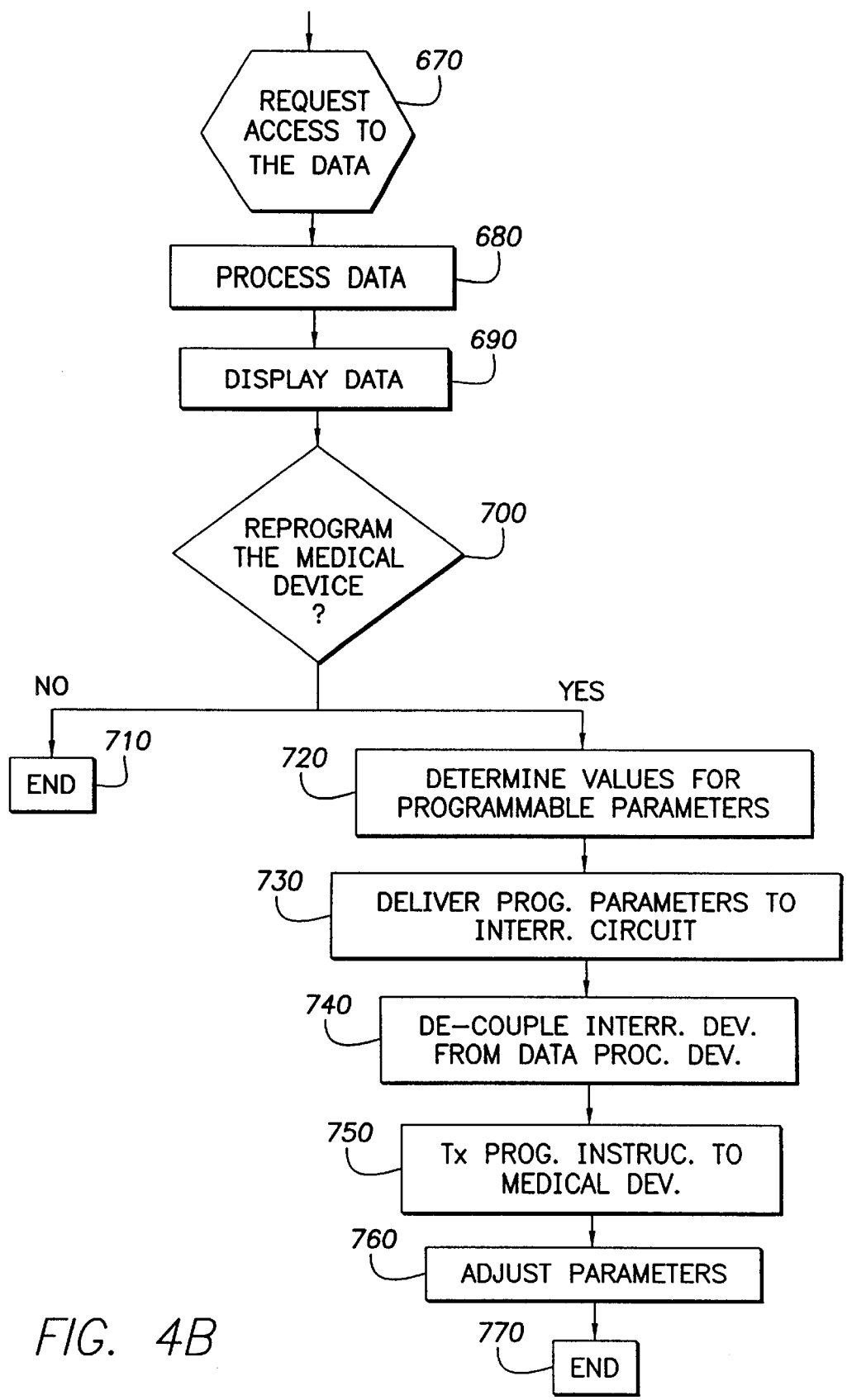
FIG. 4B is another flow diagram illustrating the operation of a portable implantable device interrogation system.

FIGS. 4A–4B are a flow diagram illustrating one implementation of a portable implantable device interrogation system 100. In step 600, an interrogation of the medical device 210 is initiated automatically or manually, such as by a patient activating an input at the portable interrogation device 230. The portable interrogation device 230 formats the appropriate interrogation instructions for telemetric transmission and transmits the instructions to the medical device 210 in step 610, using telemetry. In step 620, the medical device 210 receives the interrogation instructions requesting particular data from the medical device. The processor 270 of the medical device 210 responds to the request and in step 630, directs the acquisition and delivery of the data requested to the medical device's telemetry protocol logic circuit 330. The data requested may already be present in the medical device's memory 310, or the data may need to be acquired by the medical device 210 upon receiving the request. Using telemetry circuit 340, the medical device 210 transmits the requested data back to the portable interrogation device 230 in step 640. The portable interrogation device 230 stores the data (step 650) for later access by a data processing device 240.

When a physician needs to access and analyze the data from the medical device 210, he operatively couples the portable interrogation device 230 to a data processing device 240, as indicated in step 660. The physician then directs the data processing device 240 to access the stored data or the stored data is accessed automatically, as indicated in step 670, and the data is delivered to a processor 510 associated with the data processing device. The processor 510 processes the data, as indicated in step 680, and the data can be displayed for immediate observation by the physician, as indicated in step 690, on display 530 associated with data processing device 240. Based on the displayed data, the physician may desire to program one or more programmable parameters of the medical device 210, as indicated in step 700. If not, the process is complete, as indicated in step 710. If one or more parameters needs to be programmed, the value of the parameter(s) are determined using the data processing device 240, as indicated in step 720, and are implemented in programming instructions.

The programming instructions are formatted for delivery to the portable interrogation device 230, and delivered to the portable interrogation device through the electronic communications interfaces 470 and 500, as indicated in step 730. The telemetry head 400 of the portable interrogation device 230 is then placed near the patient near the implantable medical device 210 in preparation for a telemetric transmission. Proper placement of telemetry head 400 may include decoupling the portable interrogation device 230 from the data processing device 240, as indicated in step 740. As indicated in step 750, the portable interrogation device 230 transmits telemetrically the programming instructions to the medical device 210, and the programming instructions are formatted for use by the medical device's processor 270. The processor 270 then directs the appropriate adjustment to the medical device's programmable parameters in accordance with the programming instructions, as indicated in step 760, and the process is complete at step 770.

A number of embodiments of the present invention have been described. Nevertheless, it will be understood that various modifications may be made without departing from the spirit and scope of the invention. Accordingly, other embodiments are within the scope of the following claims.

What is claimed is:

1. A system for the communication of medical data between an implantable medical device and a data processing device, comprising:

an implantable medical device that transmits medical data by wireless communication at a first data transmission speed via a first communication path;

a portable interrogation device that receives the medical data transmitted by the implantable medical device, the portable interrogation device transferring at least a portion of the stored medical data at a second data transmission speed higher than the first data transmission speed via a second communication path; and a data processing device, coupled to the second communication path, that receives the stored medical data transmitted by the portable interrogation device at the second data transmission speed, and processes the received medical data for analysis by a physician.

2. The system of claim 1, wherein the portable interrogation device includes memory that stores at least a portion of the medical data received from the implantable medical device.

3. The system of claim 1, wherein the portable interrogation device includes a processor that generates an interrogation signal, the portable interrogation device transmitting the interrogation signal by wireless communication, wherein the implantable medical device is responsive to the interrogation device to transmit the medical data at the first transmission speed.

4. The system of claim 1, wherein the implantable medical device transmits the medical data with a first data format, and the portable interrogation device transmits the medical data with a second data format.

5. The system of claim 1, wherein the second data transmission speed is at least one thousand times greater than the first data transmission speed.

6. The system of claim 1, wherein the second data transmission speed is at least one hundred times greater than the first data transmission speed.

7. The system of claim 1, wherein the second data transmission speed is at least ten times greater than the first data transmission speed.

8. The system of claim 1, wherein the portable interrogation device being selectively connectable to the data processing device for transmission of at least a portion of the medical data.

9. The system of claim 1, wherein the second communication path conforms to the RS-232 standard.

10. The system of claim 1, wherein the portable interrogation device includes removable data storage media that stores the data transmitted by the implantable device.

11. The system of claim 10, wherein the data processing device includes a drive for receiving the removable storage media.

12. The system of claim 1, wherein the portable interrogation device includes a circuit that acquires ECG data from a patient.

13. The system of claim 12, wherein the portable interrogation device includes a circuit that synchronizes the ECG data with marker data and electrogram data obtained from the patient.

14. The system of claim 1, wherein the portable interrogation device includes a first connector and the data processing device includes a second connector that corresponds to the first connector to operatively couple the portable interrogation device with the data processing device.

15. The system of claim 1, wherein the implantable medical device is a cardiac stimulating device.

16. The system of claim 15, wherein the medical data comprises physiological data relating to cardiopulmonary function.

17. The system of claim 15, wherein the medical data comprises operational parameters of the implantable medical device.

18. The system of claim 15, wherein the medical data comprises information on the status of internal programmable parameters of the cardiac stimulating device.

19. The system of claim 15, wherein the medical data indicates the occurrence of physiological events and the responses of the cardiac stimulating device thereto.

20. The system of claim 1, wherein the portable interrogation device includes a display for displaying the data after it is received from the implantable medical device.

21. A portable medical data communications device for delivering data from an implantable medical device to a data processing device, the portable medical data communications device comprising:
- a control circuit that controls wireless transmission of interrogation instructions to an implantable medical device;
- a transmitter that transmits the interrogation instructions to the implantable medical device upon direction of the control circuit;
- a receiver that receives data transmitted by the implantable medical device in response to the interrogation instructions, the data being transmitted by wireless communication at a first data transmission speed;
- a memory associated with the receiver that stores the data received from the implantable medical device; and
- an electronic communications interface associated with the receiver that delivers at least a portion of the stored data to a data processing device, the delivery of the stored data occurring at a second data transmission speed higher than the first data transmission speed.

22. The portable medical data communications device of claim 21, wherein the portable medical data communications device receives the medical data with a first data format and the portable medical data communications device transmits the medical data with a second data format.

23. The portable medical data communications device of claim 21 wherein the electronic communications interface communicates the data to the data processing device using a wired communications path.

24. The portable medical data communications device of claim 21, wherein the portable medical communications device delivers the data to the data processing device by wireless transmission.

25. The portable medical data communications device of claim 21, further comprising:
- a telemetry circuit that formats the interrogation instructions for telemetric transmission; and
- a telemetry head that telemetrically transmits the formatted instructions to the implantable medical device and receives the data from the implantable medical device.

26. The portable medical data communications device of claim 25, wherein the telemetry head is included in a telemetry wand external to the portable medical data communications device, the telemetry wand being connected to the portable medical data communications device by a wire.

27. The portable medical data communications device of claim 26, further comprising a detector circuit that detects when the telemetry wand is in a suitable position relative to the implantable medical device to transmit the interrogation instructions or receive the data.

28. The portable medical data communications device of claim 25, wherein the telemetry head is internal to the portable medical data communications device.

29. The portable medical data communications device of claim 21, further comprising:
- a battery that powers the portable medical data communications device; and
- a battery indicator that notifies a patient of the status of power of the battery.

30. The portable medical data communications device of claim 21, wherein the memory for storing the data received from the implantable medical device includes a RAM circuit.

31. The portable medical data communications device of claim 21, further comprising a rewritable memory for storing the interrogation instructions.

32. The portable medical data communications device of claim 31, wherein the portable medical data communications device stores in the rewritable memory programming instructions for setting operational parameters of the implantable medical device, the programming instructions being delivered to the portable medical data communications device by the data processing device using a communications bus, and the programming instructions being transmitted to the implantable medical device by the portable medical data communications device using the transmitter.

33. The portable medical data communications device of claim 21, further comprising a circuit for acquiring ECG data from the patient.

34. The portable medical data communications device of claim 33, further comprising a display for displaying the ECG data after it is acquired.

35. The portable interrogation device of claim 33, further comprising a circuit that synchronizes the ECG data with marker data and electrogram data obtained from the patient.

36. A method of communicating medical data comprising:
- transmitting interrogation instructions from a portable medical data communications device to an implantable medical device using wireless communication;
- based on the interrogation instructions, receiving medical data from the implantable medical device at the portable medical data communications device at a first data transmission speed using wireless communication;
- storing the medical data in a memory at the portable medical data communications device; and
- based on a request to access the stored medical data by a data processing device operatively coupled to the portable medical data communications device by an electronic communications interface, delivering at least a portion of the stored medical data to the data processing device at a second data transmission speed higher than the first data transmission speed.

37. The method of claim 36, wherein the portable medical data communications device formats the interrogation instructions for telemetric transmission and the first data transmission speed is a speed associated with communication using wireless telemetry.

38. The method of claim 36, wherein the portable medical communications device delivers at least a portion of the stored medical data to the data processing device using a wired communication interface and the second data transmission speed is a speed associated with communication using the wired communication interface.

39. The method of claim 36, further comprising transmitting programming instructions from the portable medical data communications device to the implantable medical device, the programming instructions setting an operational parameter of the implantable medical device.

40. The method of claim 39, further comprising generating the programming instructions based on a message sent from the data processing device to the portable medical data communications device using an electronic communications bus.

41. The method of claim 40, further comprising generating the message sent from the data processing device to the portable medical data communications device based on a result of the data processing device processing the stored medical data received by the data processing device.

42. The method of claim 36, further comprising displaying on a display at least a portion of the medical data received from the implantable medical device.

43. The method of claim 42, further comprising:

prior to delivering at least a portion of the stored medical data to the data processing device, transmitting further interrogation instructions from the portable medical data communications device to the implantable medical device based on an input by a patient;

receiving further medical data at the portable medical data communications device; and storing in the memory the further medical data received.

44. A portable medical data communications device for retrieving data from an implantable medical device, the portable medical data communications device comprising:

a processor that controls transmission of instructions to an implantable medical device;

a transmitter that transmits by wireless telemetry the instructions to the implantable medical device upon direction of the processor;

a receiver that receives by wireless telemetry data transmitted by the implantable medical device in response to the instructions, the data being transmitted at a first data transmission speed;

a memory associated with the receiver that stores the data received from the implantable medical device; a data processing device for processing data from the implantable medical device; and a wired communication interface that operatively couples the memory to the data processing device, the wired communication interface being used for delivering at least a portion of the stored data from the memory to the data processing device at a second data transmission speed higher than the first data transmission speed.

* * * * *